United States Patent
Morrissey et al.

(10) Patent No.: US 6,231,845 B1
(45) Date of Patent: May 15, 2001

(54) AFTER SHAVE COMPOSITION CONTAINING ALUMINUM CHLOROHYDRATE

(75) Inventors: Maureen Sullivan Morrissey, Belmont, MA (US); Richard E. Stafford, Arlington, VA (US)

(73) Assignee: The Gillette Company, Boston, MA (US)

( * ) Notice: Subject to any disclaimer, the term of this patent is extended or adjusted under 35 U.S.C. 154(b) by 0 days.

(21) Appl. No.: 09/317,525

(22) Filed: May 24, 1999

(51) Int. Cl.$^7$ .............. A61K 7/15; A61K 9/08; A61K 9/10

(52) U.S. Cl. .............. 424/73; 424/68; 424/401; 514/937

(58) Field of Search .................. 424/73, 65, 68, 424/401

(56) References Cited

U.S. PATENT DOCUMENTS

| | | | |
|---|---|---|---|
| 4,279,891 | 7/1981 | Henkel et al. | 424/73 |
| 4,551,330 | * 11/1985 | Wagman et al. | 424/59 |
| 4,627,934 | 12/1986 | Lindauer et al. | 252/522 |
| 5,527,530 | 6/1996 | Simmons et al. | 424/401 |
| 5,665,339 | 9/1997 | Simmons | 424/73 |
| 5,989,531 | * 11/1999 | Schamper et al. | 424/65 |

FOREIGN PATENT DOCUMENTS

| | | |
|---|---|---|
| 2332857 | 1/1975 | (DE) . |
| 0261 351 | 3/1988 | (EP) . |
| 0 571 677 A1 | 12/1993 | (EP) . |
| 79427 | 7/1982 | (RO) . |
| WO 96/03963 | 2/1996 | (WO) . |

OTHER PUBLICATIONS

Balsam & Saragin, Cosmetics Science and Technology ($2^{nd}$ ed), vol. 2, pp. 19–27 & 37 (1972).
"Harry's Cosmeticology"($7^{th}$ ed.), pp. 180–189 (1982).
Kiehl's Blue Astringent Herbal Lotion (product label) 1964.
Kiehl's For the Ladies (Unscented) . . . After Shave Lotion (product label) 1851.
Gillette Series Pacific Light After Shave Splash (product label) Jan. 1995.

* cited by examiner

Primary Examiner—James M. Spear
(74) Attorney, Agent, or Firm—Stephan P. Williams

(57) ABSTRACT

The present invention provides an after shave composition comprising, by weight, 30 to 98%, preferably 65 to 95%, most preferably 70 to 90%, water, 0 to 65%, preferably 0 to 25%, most preferably 10 to 22%, ethanol, 0.25 to 6%, preferably 1 to 5%, fragrance, 0.25 to 5%, preferably 1 to 4%, surfactant to solubilize or emulsify the fragrance, and 0.5 to 1.5% (U.S.P.), preferably 0.8 to 1.3%, aluminum chlorohydrate. Preferably, the composition will be a clear solution or microemulsion having a clarity better than 100 NTU and a viscosity less than 200 mPas. The foregoing composition provides, upon application to the skin, reduced stinging and burning, reduced redness and irritation, and a soothing effect without tackiness or other undesirable aesthetic attributes.

15 Claims, No Drawings

AFTER SHAVE COMPOSITION CONTAINING ALUMINUM CHLOROHYDRATE

BACKGROUND OF THE INVENTION

The present invention relates to an after shave composition which, upon application to the skin, provides reduced stinging and burning, reduced redness and irritation, and a soothing effect without tackiness or other undesirable aesthetic attributes.

Numerous types of after shave products are known. Many of these products have very high alcohol content (e.g. >50%), although some have low alcohol or no alcohol. Each type of formulation has its drawbacks. The high alcohol formulations tend to cause stinging and burning, while the low to no alcohol formulations tend to dry too slow and feel wet. None of these products reduces redness and irritation.

It is generally known that one may add an aluminum or zinc salt to an after shave composition to increase its astringency. See, for example, *Harry's Cosmeticoloy* and *Cosmetics, Science and Technology* (Balsam and Sagarin). A product sold under the name Kiehl's Blue Astringent Herbal Lotion contains about 5% aluminum chlorohydrate and about 27% ethanol in an aqueous base that also contains witch hazel and several other ingredients. Another product, Kiehl's For The Ladies (Unscented) Moisturizing And Conditioning After-Shave Lotion, contains about 1% aluminum chlorohydrate in an opaque, alcohol-free, fragrance-free, oil-in-water lotion that contains a long, laundry list of ingredients. None of these products have good aesthetic attributes.

It is highly desirable to provide an after shave composition which provides a combination of desirable aesthetic attributes without incurring further undesirable attributes. In particular, it is desirable to provide an after shave composition that will provide reduced stinging and burning, reduced redness and irritation, and a soothing effect without tackiness or other undesirable aesthetic attributes.

SUMMARY OF THE INVENTION

An after shave composition in accordance with the present invention comprises, by weight, 30 to 98%, preferably 65 to 95%, most preferably 70 to 90%, water, 0 to 65%, preferably 0 to 25%, most preferably 10 to 22%, ethanol, 0.25 to 6%, preferably 1 to 5%, fragrance, 0.25 to 5%, preferably 1 to 4%, surfactant to solubilize or emulsify the fragrance, and 0.5 to 1.5% (U.S.P.), preferably 0.8 to 1.3%, aluminum chlorohydrate. Preferably, the composition will be a clear solution or microemulsion having a clarity better than 100 NTU (i.e. 0–100 NTU), most preferably better than 50 NTU (i.e. 0–50 NTU), and a viscosity less than 200 mPas, most preferably less than 100 mPas. The foregoing composition provides, upon application to the skin, reduced stinging and burning, reduced redness and irritation, and a soothing effect without tackiness or other undesirable aesthetic attributes. The present invention also embraces a method of reducing irritation and redness of human skin caused by shaving comprising topically applying to human skin after shaving an after shave composition as described above.

DETAILED DESCRIPTION OF THE INVENTION

The after shave composition of the present invention is primarily an aqueous or aqueous-alcoholic solution or microemulsion containing a fragrance. The composition may comprise 0 to 65%, preferably 0 to 25%, more preferably 5 to 25%, most preferably 10 to 22%, ethanol. Any fragrance or perfume may be employed so long as it may be effectively solubilized or emulsified in the composition. The amount of fragrance will typically fall within the range of about 0.25 to 6%, preferably 1 to 5%. A surfactant is added to the composition in order to solubilize or emulsify the fragrance. The surfactant is typically a polyethoxylated and/or polypropoxylated surfactant such as, for example, PPG-26-Buteth-26 and PEG-40 Hydrogenated Castor Oil. Naturally, of course, other known fragrance solubilizing surfactants may be employed for this purpose. See, for example, U.S. Pat. No. 4,279,891, U.S. Pat. No. 5,527,530, EP 261,351, EP 571,677, and WO 96/03963, the disclosures of which are incorporated herein by reference. The amount of surfactant will typically fall within the range of about 0.25 to 5%, preferably 1 to 4%.

The after shave composition will comprise 0.5 to 1.5% (U.S.P.), preferably 0.8 to 1.3%, aluminum chlorohydrate. Aluminum chlorohydrate has the general formula $Al_2(OH)_{6-n}Cl_n$ wherein n is about 0.3 to about 5, preferably about 0.8 to about 2.5, more preferably about 1 to about 2 (such that the Al to Cl mole ratio is about 0.9:1 to about 2.1:1). These salts generally have some water of hydration associated with them, typically on the order of 1 to 6 moles per mole of salt. Aluminum chlorohydrate is generally available commercially as a nominal 50% aqueous solution (about 41% U.S.P.).

The after shave composition of the present invention may also include other cosmetic ingredients to provide desirable skin benefits or aesthetic attributes. Such ingredients may include emollients, cooling agents, preservatives, viscosity modifiers, coloring agents, moisturizing agents, skin conditioning agents, medicinal agents, etc.

The present invention may be further illustrated by the following examples in which the parts and percentages are by weight.

EXAMPLES 1 TO 6

After shave compositions are prepared having the ingredients and the amounts set out below. Each of these compositions is prepared by mixing the oil phase (fragrance, surfactant and alcohol) with the aqueous phase (aluminum chlorohydrate and water) to provide a clear solution or microemulsion.

| Ingredient | Weight Percent | | | | | |
| --- | --- | --- | --- | --- | --- | --- |
|  | Ex. 1 | Ex. 2 | Ex. 3 | Ex. 4 | Ex. 5 | Ex. 6 |
| Water | 74.50 | 72.20 | 79.00 | 74.70 | 91.50 | 34.00 |
| Ethanol | 20.00 | 22.00 | 15.00 | 20.00 |  | 60.00 |
| Alum. chlorohydrate | 1.00 | 1.30 | 1.00 | 0.80 | 1.00 | 1.00 |
| Fragrance | 2.50 | 2.50 | 2.50 | 2.50 | 2.50 | 4.50 |
| Surfactant[1] | 2.00 | 2.00 | 2.50 | 2.00 | 5.00 | 0.50 |

[1]PPG-26-Buteth-26 and PEG-40 Hydrogenated Castor Oil

What is claimed is:

1. An after shave composition comprising, by weight, 30 to 98% water, 5 to 65% ethanol, 0.25 to 6% fragrance, 0.25 to 5% surfactant to solubilize or emulsify the fragrance, and 0.5 to 1.5% (U.S.P.) aluminum chlorohydrate.

2. An after shave composition consisting essentially of, by weight, 30 to 98% water, 0 to 65% ethanol, 0.25 to 6% fragrance, 0.25 to 5% surfactant to solubilize or emulsify the fragrance, and 0.5 to 1.5% (U.S.P.) aluminum chlorohydrate.

3. The composition of claim 1 comprising 65 to 95% water and 5 to 25% ethanol.

4. The composition of claim 3 comprising 0.8 to 1.3% aluminum chlorohydrate.

5. The composition of claim 1 consisting essentially of 70 to 90% water, 10 to 22% ethanol, 1 to 5% fragrance, 1 to 4%, surfactant to solubilize or emulsify the fragrance, and 0.8 to 1.3% (U.S.P.) aluminum chlorohydrate.

6. The composition of claim 1, 3, 4 or 5 in the form of a clear solution or microemulsion having a clarity better than 100 NTU.

7. The composition of claim 6 having a viscosity less than 200 mPas.

8. The composition of claim 7 having a viscosity less than 100 mPas.

9. The composition of claim 8 having a clarity better than 50 NTU.

10. A method of reducing irritation and redness of human skin caused by shaving comprising topically applying to shaved human skin an after shave composition comprising, by weight, 30 to 98% water, 5 to 65% ethanol, 0.25 to 6% fragrance, 0.25 to 5% surfactant to solubilize or emulsify the fragrance, and 0.5 to 1.5% (U.S.P.) aluminum chlorohydrate.

11. A method of reducing irritation and redness of human skin caused by shaving comprising topically applying to shaved human skin an after shave composition comprising, by weight, 30 to 98% water, 0 to 65% ethanol, 0.25 to 6% fragrance, 0.25 to 5% surfactant to solubilize or emulsify the fragrance, and 0.5 to 1.5% (U.S.P.) aluminum chlorohydrate.

12. The method of claim 10 wherein said composition comprises 65 to 95% water and 5 to 25% ethanol.

13. The method of claim 12 wherein said composition comprises 0.8 to 1.3% aluminum chlorohydrate.

14. The method of claim 10 wherein said composition consists essentially of 70 to 90% water, 10 to 22% ethanol, 1 to 5% fragrance, 1 to 4%, surfactant to solubilize or emulsify the fragrance, and 0.8 to 1.3% (U.S.P.) aluminum chlorohydrate.

15. The method of claim 10, 12, 13 or 14 wherein said composition is in the form of a clear solution or microemulsion having a clarity better than 100 NTU and a viscosity less than 200 mPas.

* * * * *